United States Patent [19]

Weaver et al.

[11] Patent Number: 4,993,418

[45] Date of Patent: Feb. 19, 1991

[54] DOPPLER BLOOD FLOW SYSTEM AND METHOD USING LOW FREQUENCY NOISE SIGNAL PROCESSING

[75] Inventors: Billy L. Weaver, Eagan; Dirk R. Smith, St. Paul, both of Minn.

[73] Assignee: Minnesota Mining and Manufacturing Company, St. Paul, Minn.

[21] Appl. No.: 302,406

[22] Filed: Jan. 26, 1989

[51] Int. Cl.$^5$ .............................................. A61B 5/026
[52] U.S. Cl. ............................. 128/661.08; 73/861.25
[58] Field of Search ...................... 128/661.07, 661.08, 128/661.09, 661.1, 662.04, 663.01; 73/631, 861.25; 604/65

[56] References Cited

U.S. PATENT DOCUMENTS

| | | | |
|---|---|---|---|
| 3,498,290 | 3/1970 | Shaw et al. | 73/861.25 |
| 4,690,002 | 9/1987 | Hubbard | 73/861.25 |
| 4,770,184 | 9/1988 | Greene, Jr. et al. | 128/661.08 |
| 4,807,636 | 2/1989 | Skidmore et al. | 73/861.25 |
| 4,825,422 | 4/1989 | Takeda | 73/861.25 |

OTHER PUBLICATIONS

Atkinson, Peter et al., "A Fundamental Interpretation of Ultrasonic Doppler Velocimeters", *Ultrasound in Medicine & biology*, vol. 2, pp. 107-111, Pergamon Press (1976).
Newhouse et al., "The Effects of Geometric Spectrum Broadening on Ultrasonic Doppler Flow Measurement Systems", *29th ACEMB Proceedings*, p. 140 (1976).
Lunt, M. J., "Accuracy and Limitations of the Ultrasonic Doppler Blood Velocimeter and Zero Crossing Detector", *Ultrasound in Medicine and Biology*, vol. 2, pp. 1-10.
Brody, "Theoretical Analysis of the CW Doppler Ultrasonic Flowmeter", *IEEE Transactions on Biomedical Engineering*, vol. BME-2, No. 3, pp. 183-192 (1974).
Sears et al., *College Physics*, Fourth Edition, pp. 366-367, Addison-Wesley Publishing Company (1974).
Atkinson & Woodcock, *Doppler Ultrasound and its Use in Clinical Measurement*, Chapters 1 and 3, Academic Press (1982).
Murphy and Rolfe, "Application of the TMS320 Signal Processor for the Real-Time Processing of the Doppler Ultrasound Signal", *IEEE/Eighth Annular Conference of the Engineering in Medicine and Biology Society*, pp. 1175-1178 (1986).

*Primary Examiner*—Kyle L. Howell
*Assistant Examiner*—K. M. Pfaffle
*Attorney, Agent, or Firm*—Donald M. Sell; Walter N. Kirn; William D. Bauer

[57] ABSTRACT

A Doppler blood flow system and method in which an ultrasonic wave is reflected off of red blood cells in blood flowing in tubing. The reflected ultrasonic wave is digitally processed in the frequency domain. The flow rate of the blood is directly related to the average frequency of the Doppler signal. The typical Doppler signal is not a single frequency representing a single flow rate but is really an entire range of frequencies in which certain frequencies predominate which are indicated by increased amplitude of the signal when plotted in the frequency domain. The typical Doppler signal may actually have two "humps", one at a higher frequency which represents the actual information bearing content of the signal related to flow rate and one at a lower frequency which is caused by vibrations in the blood tubing system itself and could be caused by motor noise from the blood pump. Since the flow rate is related to average frequency of the information bearing portion of the typical Doppler signal, the low frequency "hump" must be taken out of the Doppler signal in order to obtain an accurate flow rate.

2 Claims, 5 Drawing Sheets

DOPPLER BLOOD FLOW SYSTEM AND METHOD USING LOW FREQUENCY NOISE SIGNAL PROCESSING

BACKGROUND OF THE INVENTION

The present invention relates generally to Doppler blood flow measurement systems and techniques, and more particularly to Doppler blood flow measurement systems and techniques using the frequency domain signal analysis.

During cardiopulmonary bypass surgery, ventricular assist using blood pumps and other cardiac surgeries, blood flow external to the patient is necessary. Known blood pumps and so-called heart-lung machines operate to transport the blood of the patient through tubing or conduits in order to perform their function. During the transportation of blood in these external (to the body of the patient) tubes or conduits, it is extremely important for the surgeon to monitor the rate of flow of the blood so that abnormalities in the flow can be detected and corrective action can be taken.

Various systems and techniques have been utilized to measure the flow of blood, or other fluids, through tubes or conduits in the past.

Invasive measurement systems including techniques such as vane type flow meters not only require either disposal or sterilization after each use, but, with blood, may lead to unwanted coagulation or other problems. U.S. patent application Ser. No. 07/074,549 Lloyd C. Hubbard and Earl W. Clausen, filed July 17, 1987, entitled FLOW MEASUREMENT SYSTEM, assigned to Minnesota Mining and Manufacturing Company who is the assignee of the present invention, describes a blood flow measurement system for use with a motor driven centrifugal pump. The system takes advantage of the fact that, at a constant speed of rotation and a constant viscosity, the torque required to drive a centrifugal pump is directly related to the flow produced by the pump. Blood flow is computed from the speed of rotation of the pump and the torque of the motor.

The use of ultrasound to determine the flow of blood in a blood vessel started generally in the 1950's. Some of these ultrasound systems were implanted into the patient and some utilized measurements taken external to the patient.

The ultrasonic measurement of blood flow through tubes or conduits using the known Doppler frequency shift effect has been utilized. Such a measurement system and technique has the distinct advantage of being non-invasive. The tube or conduit, being relatively transparent to the ultrasonic waves, need not be physically invaded. In such known systems and techniques an ultrasonic transmitter is placed angularly with respect to the expected blood flow through the tube or conduit. An ultrasonic receiver is angularly placed on the opposite or same side of the tube or conduit. The presence of particulates, such as red blood cells, air bubbles and fat globules, act as targets for the reflection of the ultrasonic signal. The velocity of these targets cause a frequency shift in the reflected ultrasonic frequency according to the well known Doppler effect.

An example is a prior flowmeter marketed by Sarns, Inc. of Ann Arbor, Mich. (now a subsidiary of Minnesota Mining and Manufacturing Company, St. Paul, Minn., the assignee of the present application) known as the Sarns model 7800 flowmeter. An accuracy of about ± ten percent (10%) was achievable with this device. Indeed, in order to achieve this accuracy the console of each flowmeter must be matched to an individual flow-probe at the time of manufacture. Due to the matching requirement, manufacturing and field service was made more difficult and interchangeability of probes between flowmeters could not be achieved.

The system described in U. S. Pat. No. 4,690,002, Hubbard et al, also assigned to Minnesota Mining and Manufacturing Company, is an example of an ultrasonic Doppler blood flow measurement system. This system operates on an analog basis by amplifying the reflected signal, clipping it, using automatic gain control to restrain the signal into a reasonably finite range and converting the signal from a frequency to a voltage by use of an analog frequency-to-voltage converter.

In Atkinson, Peter, "A Fundamental Interpretation of Ultrasonic Doppler Velocimeters", *Ultrasound in Medicine & Biology*, Volume 2, pp. 107-111, Pergamon Press (1976) a description is provided for basic Doppler velocimeters and their usefulness in medical and industrial fields. Atkinson notes that in useful Doppler systems, as opposed to theoretical systems, that the received signal will exhibit a range of Doppler difference spectrum rather than a single frequency predicted by a perfect system. This range of spectrum will be exhibited by a "hump" or bell-shaped curve in the frequency domain. The cause may be the propagation of a finite width beam as opposed to an arbitrarily narrow pulse or may be caused by a finite length of pulse in a pulsed system as opposed to an infinitely short pulse. Atkinson also discloses that the reflection (backscatter) from blood will be amplitude modulated due to differences in time of the volume of red blood corpuscles.

An article by Newhouse et al, "The Effects of Geometric Spectrum Broadening On Ultrasonic Doppler Flow Measurement Systems", *29th ACEMB Proceedings*, p. 140 (1976) discusses that spectrum broadening in ultrasonic Doppler flow systems is due to geometric broadening.

An article by Lunt, M. J., "Accuracy and Limitations of the Ultrasonic Doppler Blood Velocimeter and Zero Crossing Detector", *Ultrasound in Medicine and Biology*, Volume 2, pp. 1-10 (1975), discusses the use of zero crossing detectors in ultrasonic Doppler blood flow measurement.

An article by Brody, "Theoretical Analysis of the CW Doppler Ultrasonic Flowmeter", *IEEE Transactions on Biomedical Engineering*, Volume BME-2, No. 3, pp. 183-192 (1974) discusses the theoretical basis for ultrasonic continuous wave Doppler blood flowmeters.

A portion of a Chapter from Sears et al, *College Physics*, Fourth Edition, pp. 366-367, Addison-Wesley Publishing Company (1974) describes the basic Doppler effect as related to acoustic phenomenon.

A book by Atkinson & Woodcock, *Doppler Ultrasound and its Use in Clinical Measurement*, Chapters 1 and 3, Academic Press (1982) provides an introduction into Doppler sound wave theory and its reaction to the measurement of blood and exemplary systems for the processing and analysis of Doppler shift signals. This books provides a good discussion of the conversion of the Doppler from the time domain to the frequency domain.

An article by Murphy and Rolfe, "Application of the TMS320 Signal Processor for the Real-Time Processing of the Doppler Ultrasound Signal", *IEEE/Eighth Annual Conference of the Engineering in Medicine and Biol-* ogy Society, pp. 1175-1178 (1986) describes techniques to achieve real-time processing of Doppler ultrasound signals applied to the measurement of blood flow. Murphy et al uses Fast Fourier Transform (FFT) techniques to convert from the time domain to the frequency domain and to digitally obtain the average frequency which corresponds to the blood flow measured.

SUMMARY OF THE INVENTION

In order to properly determine the rate flow of the blood flowing in tubing, a proper analysis of the characteristics of the incoming Doppler signal must be made. The typical Doppler signal is not a single frequency representing a single flow rate but because of a number of reasons relating to particle size, a typical Doppler signal is really an entire range of frequencies in which certain frequencies predominate which are indicated by increased amplitude of the signal when plotted in the frequency domain. The typical Doppler may actually have two "humps", one at a higher frequency which represents the actual information bearing content of the signal related to flow rate and one at a lower frequency which is caused by vibrations in the blood tubing system itself and could be caused by motor noise from the blood pump or other soundwaves in the area. Since the flow rate is related to average frequency of the information bearing portion of the typical Doppler signal, to take the actual average frequency of a typical Doppler signal could result in an inaccurate result.

The apparatus and method of the present invention eliminate this inaccurate result by eliminating the low frequency hump before determining the average frequency of the Doppler signal and, hence, the flow rate of the blood.

The present invention provides a method of determining the rate of flow of a fluid containing particles flowing through a tube. First, the method transmits an ultrasonic signal through the tube at an oblique angle thereto. The ultrasonic signal which has been reflected off of the particles contained in said fluid is received as a received ultrasonic signal. The received ultrasonic signal is then filtered to remove the low frequency components therefrom creating a filtered ultrasonic signal. The rate of flow of said fluid is then calculated from said filtered ultrasonic signal using Doppler techniques.

It is preferred that the calculating step utilize the step of determining the average frequency of the filtered ultrasonic signal.

The present invention also provides a method of determining the rate of flow of a fluid containing particles flowing through a tube. An ultrasonic signal is transmitted through the tube at an oblique angle thereto. The ultrasonic signal which has been reflected off the particles contained in said fluid is received as a received ultrasonic signal. The received ultrasonic signal is then converted from the time domain into the frequency domain creating a frequency domain signal. The frequency domain signal is then analyzed for a low frequency hump noise component. The low frequency hump is removed from the frequency domain signal creating a modified frequency domain signal. The average frequency of said modified frequency domain signal is determined. The rate of flow of said fluid is calculated from said average frequency of said modified frequency domain signal using Doppler techniques.

The present invention also provides an apparatus for determining the rate of flow of a fluid containing particles flowing through a tube. An ultrasonic signal transmitter is arranged to transmit an ultrasonic signal through the tube at an oblique angle thereto. A receiver is arranged to receive the ultrasonic signal which has been reflected off of the particles contained in the fluid having a received ultrasonic signal as an output. A filter is coupled to the received ultrasonic signal to remove the low frequency noise components therefrom creating a filtered ultrasonic signal. A calculation mechanism is coupled to the filtered ultrasonic filter for calculating the rate of flow of the fluid from the filtered ultrasonic signal using Doppler techniques.

Preferably a frequency mechanism is coupled between the filter and the calculation mechanism for determining the average frequency of the filtered ultrasonic signal and wherein the calculation mechanism determines the rate of flow of the fluid by using the average frequency of the filtered ultrasonic signal obtained from the frequency means.

The present invention also provides an apparatus for determining the rate of flow of a fluid containing particles flowing through a tube. An ultrasonic signal transmitter is arranged to transmit an ultrasonic signal through the tube at an oblique angle thereto. A receiver is arranged to receive the ultrasonic signal which has been reflected off of the particles contained in the fluid having a received ultrasonic signal as an output. A converter is coupled to the received ultrasonic signal for converting the received ultrasonic signal from the time domain into the frequency domain creating a frequency domain signal. An analyzer is coupled to the frequency domain signal for analyzing the frequency domain signal for a low frequency noise hump. A signal processor is coupled to the analyzer for removing the low frequency hump from the frequency domain signal creating a modified frequency domain signal. A determining mechanism is coupled to the signal processor for determining the average frequency of the modified frequency domain signal. A calculating mechanism is coupled to modified frequency domain signal for calculating the rate of flow of the fluid from the average frequency of the modified frequency domain signal using Doppler techniques.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Modern digital blood flowmeters rely on the well known Doppler effect to make accurate measurements on the flow of blood in a tube, or conduit, external to the patient. The Doppler technique relies on the interaction between a series in incident sound waves against moving particles in the blood. A common example of the Doppler effect is drop in pitch of a car horn as you pass a car moving in the opposite direction. In its most basic form, the Doppler principle states that if a receiver moves relative to the source then the frequency of the sound as seen by the receiver is not the same as the frequency sent out by the source. If the receiver moves toward the source then the frequency is shifted up, and if the receiver moves away from the source then the frequency is shifted down.

In the case of a blood flowmeter, both the source and the receiver are stationary, while the sound is reflected off of a moving target (particles in the blood). The moving target then acts as the moving source transmitting at a shifted frequency from the original source. The receiver then picks up the reflected signal having been shifted in frequency.

Human blood is composed of a liquid called plasma, red blood cells, white blood cells and platelets. The red blood cell is a biconcave disc with an average diameter of about 7 microns and an average thickness of about 2 microns. The mean volume of a red blood cell is about 90 cubic microns and there approximately 5,000,000,000 red blood cells per cubic millimeter of blood. This concentration corresponds to a haematocrit of about forty-five percent (45%). The number of white blood cells is relatively small, namely about 7,500. The platelets are much smaller than the red blood cells.

As the sound wave is reflected from the moving blood, the sound wave (signal) is generally scattered. Because the red blood cells are much larger than the platelets and much more numerous than the white blood cells, they are the major cause of scattering in the reflected sound wave (signal). This scattering is a random process. This random process obeys the Rayleigh scattering law, namely that if the particle size is much less than the wavelength of the incident wave (in this case $7 \times 10^{-6}$ meters particle size versus a wavelength in blood of $3.75 \times 10^{-4}$ meters for a 4 megaHertz ultrasound source) the particle becomes a point source. The wavelength of the ultrasound signal is about 100 times larger than the red blood cell, therefore the red blood cell acts as a point scatter to the incident sound wave. Further, the scattering process will be governed by the Poisson probability distribution.

Figure 1:
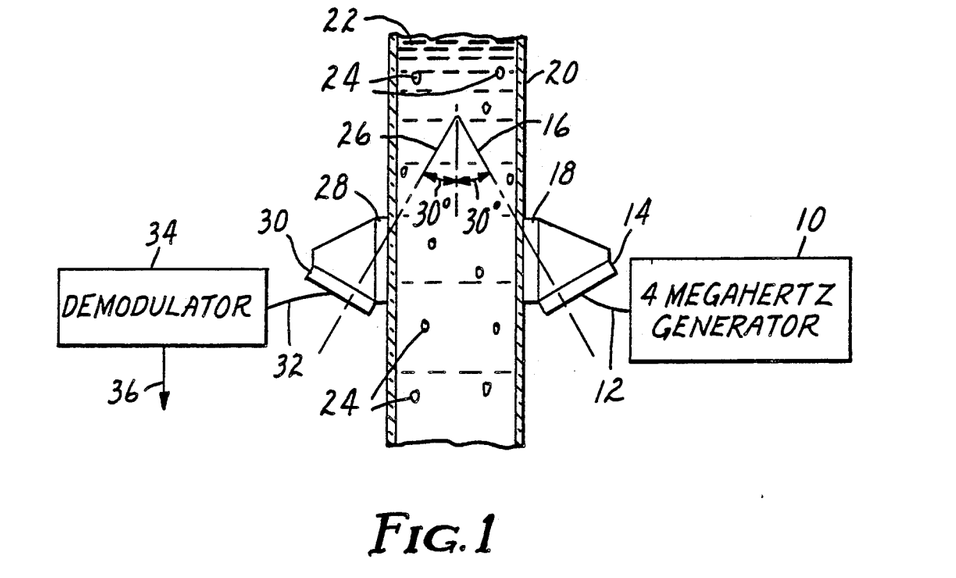
FIG. 1 is an illustration of the ultrasonic transmission and reception portion of the Doppler blood flow system of the present invention (portions of which are shown in section for clarity)

As can be seen by reference to FIG. 1, the source 10, an oscillator or a 4 megaHertz signal generator, produces a 4 megaHertz sinusoidal waveform 12 which is applied to a piezoelectric crystal 14 which produces a 4 megaHertz ultrasonic wave 16. This ultrasonic wave 16 is transmitted through an acrylic "lens" 18 to the surface of tubing 20, or conduit, containing the flowing blood 22. The "lens" 18 allows the attachment of the piezoelectric crystal 14 to the wall of tubing 20 so that the ultrasonic wave 16 makes an oblique angle with the flowing blood 22. Preferably this angle is approximately thirty degrees (30°). The ultrasonic wave 16 then enters the blood 22 flowing through the wall of the tubing 20. The red blood cells 24 in the blood 22 then reflect and backscatter the ultrasonic wave 16 (transmitted signal). These red blood cells 24 act as small "transmitters", transmitting a reflected ultrasonic wave 26 which has been shifted in frequency. Some of the reflected or backscattered wave 26 passes back through the wall of tubing 20, through another acrylic "lens" 28 to another piezoelectric crystal 30 which converts the reflected ultrasonic wave 26 into an electric signal 32. "Lens" 28 also allows the attachment of piezoelectric crystal 30 to the wall of tubing 20 at an oblique angle thereto. Preferably this angle is equal to the angle made by "lens" 18, and preferably is approximately thirty degrees (30°). The frequency of the signal 32 at this point consists of the original 4 megaHertz ultrasonic signal 12 plus (or minus) the frequency shift due to the Doppler effect. Signal 32 is then passed to demodulator 34 which separates the portion of the signal 32 containing the frequency shift from the original 4 megaHertz transmitted signal 12. Thus the output 36 of demodulator 34 consists only of the frequency shift due to moving flow of blood 22 through tubing 20.

The parts illustrated in FIG. 1, including the generator 10, piezoelectric crystal 14, lens 18, tubing 20, lens 28, piezoelectric crystal 30 and demodulator 34 are well known in the art. These parts are identical in a Doppler flowmeter using analog signal processing techniques marketed by the Sarns, Inc. subsidiary of Minnesota Mining and Manufacturing Company, the assignee of the present invention, under Model No. 7800. The system described in U. S. Pat. No. 4,690,002, Hubbard et al, also assigned to Minnesota Mining and Manufacturing Company, also discloses an ultrasonic Doppler blood flow measurement system utilizing the components described in FIG. 1, and is hereby incorporated by reference.

The received and demodulated signal 36 has been "Doppler shifted" and the average frequency of this signal is linearly related to rate of flow of blood 22 in tubing 20. In the preferred flowmeter system, the average frequencies range from 0 to 5 kiloHertz which correspond to flow rates of from 0 to 8 liters per minute (LPM).

Theoretically, the received and demodulated signal 36 would be a single frequency representing the rate of flow of the blood 22. This single frequency result can only be achieved if several restrictions are met. An infinitely wide plane target must move at constant velocity through a monochromatic ultrasonic field which has an infinite beam width and if all targets were moving at the same velocity. In practice, of course, this does not occur. The result in practice is a signal which over time produces components of varying amplitude and varying frequency. As a result the signal 36 containing the Doppler information must be further processed in order to properly extract the frequency information indicative of the rate of blood flow.

Figure 2:
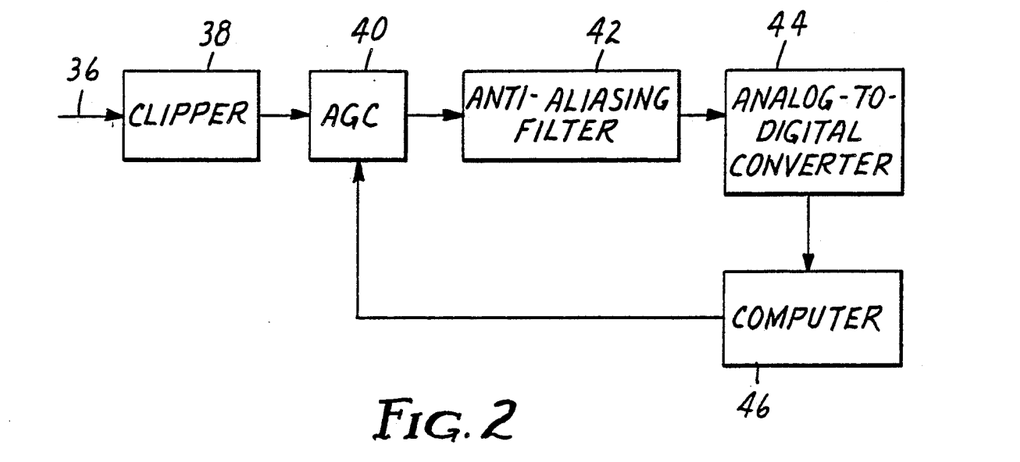
FIG. 2 is a block diagram of the signal processing portion of the Doppler blood flow system of the present invention.

This processing occurs in the circuitry illustrated in FIG. 2. The Doppler output signal 36 from FIG. 1 is supplied to a clipping circuit 38, preferably a diode clipping circuit. Since the blood 22 may contain air bubbles or significant concentrations of red blood cells 24 which would produce a reflected wave 26 and subsequent Doppler output signal 36 which would be of significantly increased magnitude. In order to limit the Doppler output signal 36 so that subsequent circuitry may properly process it, the signal 36 is clipped by clipping circuit 38 to limit its maximum amplitude. Clipping circuit 38 is conventional in nature and is also contained in the Sarns Model No. 7800 flowmeter.

The clipped signal is then supplied to AGC circuit 40 which provides automatic gain control. The AGC circuit 40 is preferably a SC11310CN by Sierra Semiconductor. AGC circuits are conventional in Doppler systems in order to provide automatic gain control of the signal to be processed. Conventional automatic gain control circuits operate by sensing the amplitude of the received signal and adjusting their gain accordingly. As will be seen in the subsequent description, AGC circuit 40 operates under software control. That is, the software determines the gain which the AGC circuit 40 provides. While this is the preferred embodiment of AGC circuit 40, it is within the contemplation of the present invention that a conventional real-time amplitude controlled AGC 40 circuit could be utilized.

The signal is then supplied to an anti-aliasing filter 42 and is digitized by analog-to-digital converter 44 which includes a sample and hold circuit. Anti-aliasing filters in connection with Doppler systems are conventional in nature and well known in the art. It is preferred that anti-aliasing filter 42 be a HSCF24040ACJ by Honeywell. This circuit allows the characteristics of the filter to be set under software control according to well known and conventional criteria. Although preferred it is within the contemplation of the present invention that a conventional non-software controlled anti-aliasing filter could be utilized. The preferred analog-to-digital converter 44 is a CSZ5112-KJ12 by Crystal Semiconductor. This analog-to-digital converter 44 is a 12-bit converter which gathers data samples at a rate of 41.67 kiloHertz. Again A-to-D converters are conventional in Doppler systems and any of a variety of A-to-D converter circuits could be employed here.

Once the Doppler signal has been converted to digital format in analog-to-digital converter 44, the signal may be processed digitally by computer 46. The preferred computer 46 includes a model TMS320C25 16-bit digital signal processor by Texas Instruments. The purpose of computer 46 is to extract the frequency information from the digital Doppler signal so that the rate of blood flow may be determined. While generally the use of a computer 46 to extract the rate of blood flow information from the digital Doppler is well known in the art, the particular routines utilized in the methods and apparatus of the present make the information extracted particularly accurate and useful. It is the particular subroutines utilized in the digital signal processing which is the essence of the present invention. The general ability to convert the digital Doppler signal to a rate of blood flow is known.

While the digital Doppler signal contains the information relating to the rate of flow of blood 22 through tubing 20, the digital Doppler signal also contains other information, particularly noise which make the analysis of the digital Doppler particularly difficult. The goal of the present flowmeter system and method is to calculate flow rates with a ± ten percent (10%) accuracy from 0.7 to 7.0 liters per minute. To allow interchangeability of probes (the Doppler transmitting and receiving hardware described in FIG. 1) the calculation software allows for the receipt of "probe characterization numbers" to calibrate the calculations for individual probes, as the relationship between average frequency and flow rate may be different for different probes.

Figure 3:
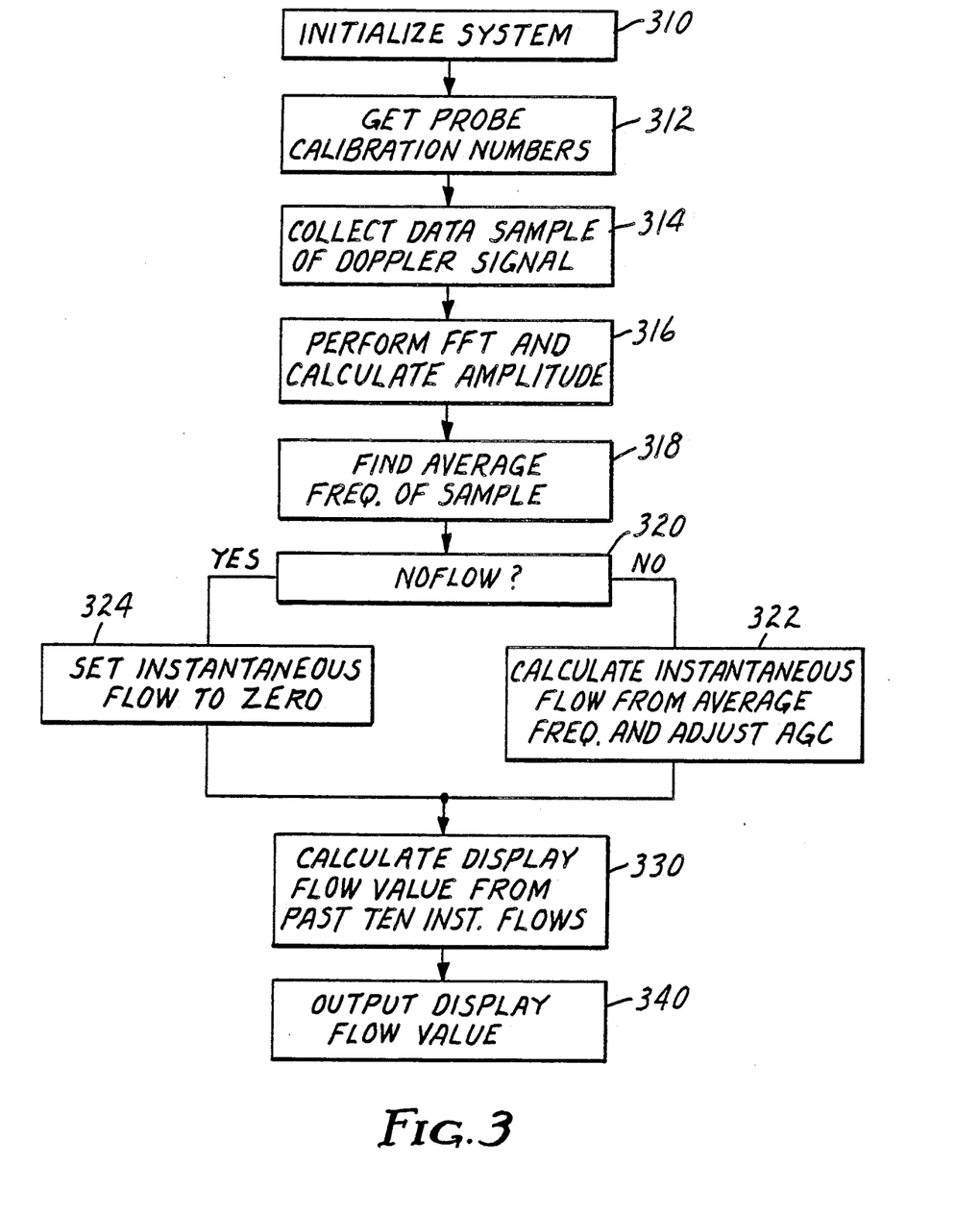
FIG. 3 is a flow chart of the main software algorithm associated with the apparatus and method of the present invention.

The basic algorithm performed by the software of computer 46 is illustrated in FIG. 3. The software gathers the digital samples of the digitized Doppler signal, calculates the average frequency of the signal and then converts this frequency to a flow rate based upon a known, linear relationship between average frequency and the rate of flow. The software also performs averaging of past data samples to determine an accurate and stable flow reading and, as will be seen below, includes steps to determine if the special case of zero flow exists. The preferred software embodiment of this main program loop is shown in Attachment A.

After initialization 310, which simply involves preparation of look-up tables according to well known techniques, the main loop of the program begins and is performed continuously until the computer 46 is reset. The preferred software embodiment of the initialization step 310 is shown in Attachments B and C. First the "probe characterization number" is read 312 to adjust the calculations to the particular probe being utilized. The preferred embodiment of receiving the probe characterization numbers is shown in Attachment D. The digital waveform is then obtained 314 by collecting a 1024 point sample of the incoming Doppler signal from the analog-to-digital converter 44. The waveform is then converted 316 into the frequency domain by Fast Fourier Transform (FFT) to calculate the frequency distribution of the signal. The preferred embodiment of the data sampling and FFT calculation steps is shown in Attachment E. In addition, the actual amplitude of the incoming signal is also calculated from the 1024 data points and stored in a table containing the amplitudes of the past 10 samples. This amplitude data is utilized later in a special subroutine related to zero flow detection. Next, the average frequency of the Doppler signal is calculated 318 from the FFT results (this calculation subroutine is described later in reference to FIG. 6). Unless a zero flow condition exists 320, which will be described in conjunction with FIG. 7, the instantaneous flow rate is calculated 322 based upon the average frequency of the sample and the probe characterization numbers. If a zero flow condition exists, then the instantaneous flow rate is set 324 to zero.

The instantaneous flow rate calculation 322 is calculated by first subtracting the intercept value from the average frequency and then dividing the result by the slope value.

In addition to calculating 322 the instantaneous flow rate, the power level of the incoming signal is analyzed and, based upon the power level of the incoming signal, a new gain value is supplied to the AGC circuit 40. The maximum and minimum voltages which can be measured by the preferred analog-to-digital converter 44 are ±2.5 volts. The AGC circuit 40 can be software controlled by being sent an integer between 0 and 255 (8-bits) corresponding to a gain or loss of 0 to 25.5 dB. The ninth bit of data indicates whether gain or loss is desired. The automatic gain is controlled by measuring the average absolute value amplitude of the sampled signal to a constant which represents the target signal strength. If the measured signal is less than the target, the gain is increased by 0.5 dB and if the measured signal is greater than the target, the gain is decreased by 0.5 dB. The 0.5 dB increase or decrease in gain corresponds to an increase or decrease of 5 in the integer value sent to the AGC circuit 40 by the software. The probe characterization numbers used in this calculation represent the slope and intercept values of a plot of average frequency versus flow rate for a particular probe. They are predetermined in manufacture by measuring the average frequency at various flow rates for each individual probe, and then performing a least square linear fit on the data.

The instantaneous flow rate is averaged 330 over the past ten instantaneous flow rates. If the averaged flow rate then differs by more than 0.1 liters per minute then the display (or output) may be updated. Otherwise the display (or output) is not updated to prevent needless "toggling" of the output data. This averaged flow rate (display flow rate) may be displayed 340 or otherwise utilized.

Figure 4:
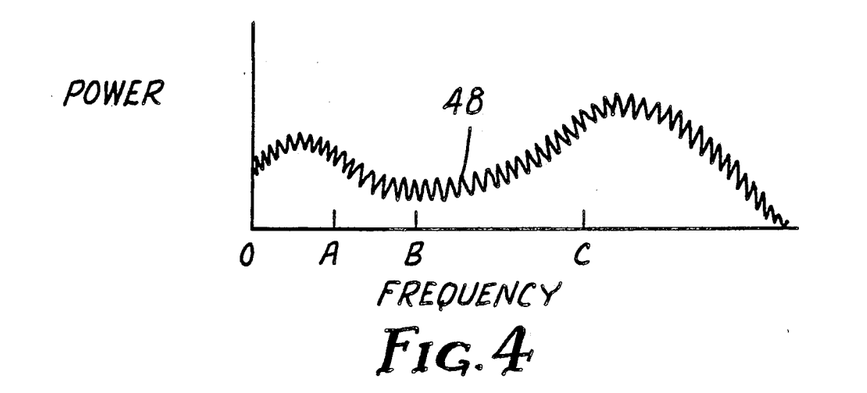
FIG. 4 is a graph of an exemplary raw Doppler signal.

In order to properly determine the rate flow of the blood 22 flowing in tubing 20, a proper analysis of the characteristics of the incoming Doppler signal must be made. FIG. 4 illustrates a typical Doppler signal 48 in the frequency domain. The chart of FIG. 4 is a plot of the Doppler signal with frequency as the horizontal axis and amplitude (or power) as the vertical axis. As can be seen the signal 48 is not a single frequency representing the flow rate but because of a number of reasons including those discussed above relating finite wave width and particle size signal 48 is really an entire range of frequencies in which certain frequencies predominate (illustrated by increased magnitude of the signal or "humps"). Signal 48 has actually two "humps", one at a higher frequency which represents the actual information bearing content of the signal related to flow rate and one at a lower frequency which is caused by motor noise from the blood pump (not shown) or other vibrations. Since the flow rate is related to average frequency of the information bearing portion of the signal 48, to take the actual average frequency of signal 48 would result in frequency C in FIG. 4. Since this average frequency is influenced by the low frequency "hump" caused by motor or pump noise, an inaccurate result is obtained.

Figure 5:
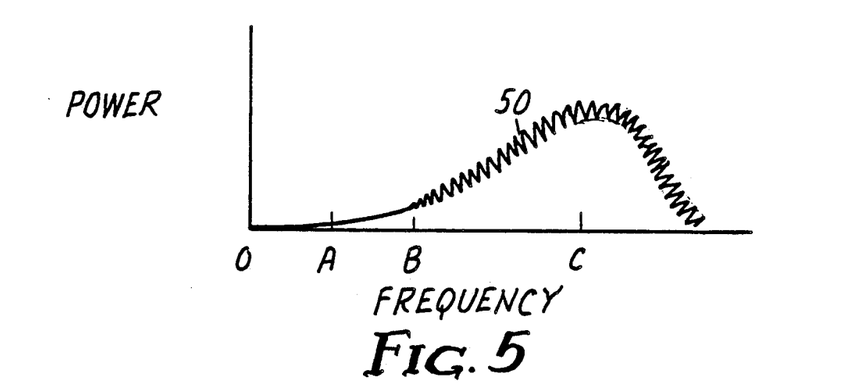
FIG. 5 is a graph of the exemplary Doppler signal of FIG. 4 having been processed according to one of the aspects of the present invention.

In order to eliminate the low frequency "hump" in FIG. 4, the software calculates the average frequency 40 of signal 48 and then divides that average frequency by 4 to obtain frequency A in FIG. 4. In general the low frequency "hump" noise is contained within the range from zero to frequency A. The software then makes a piece-wise exponential estimation of the Doppler signal ignoring the low frequency "hump" below frequency A. In order smooth the Doppler signal in the low frequency range the curve is estimated and smoothed between the frequency range of zero and the average frequency (Frequency C) divided by 2 (Frequency B). The result of this software elimination of the low frequency noise "hump" is shown by the modified signal 50 illustrated in FIG. 5.

Figure 6:
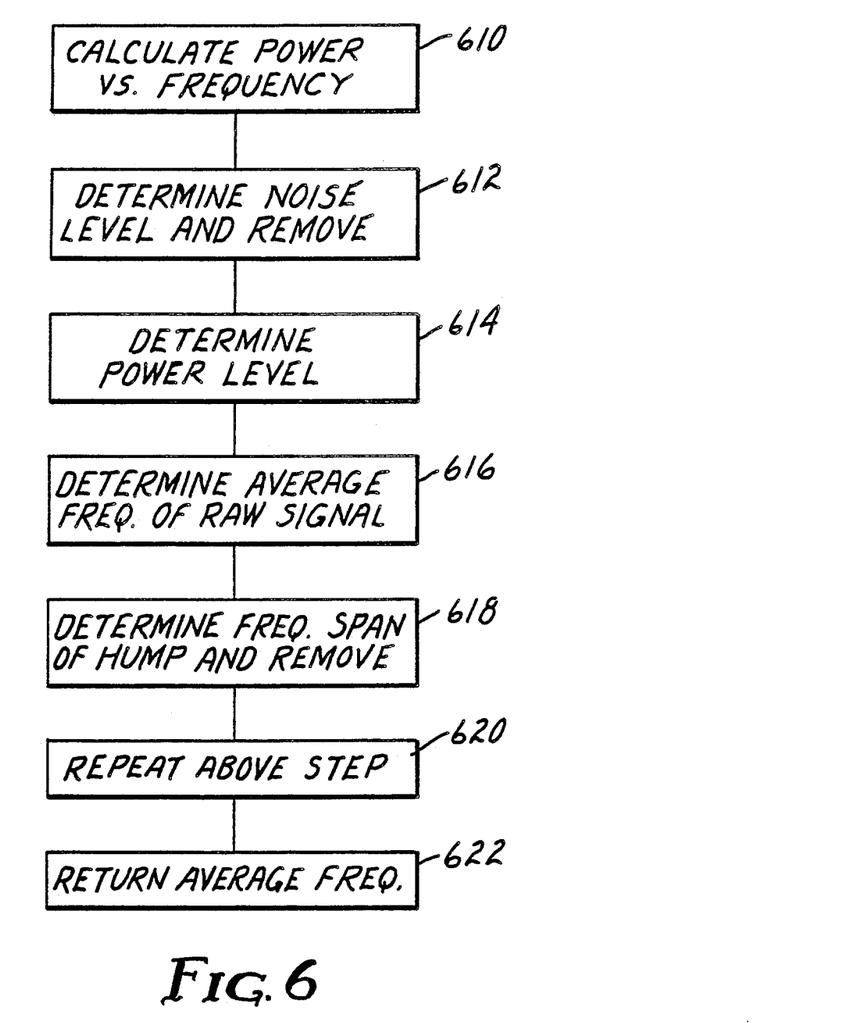
FIG. 6 is a flow chart of a portion of the software algorithm associated with the determination of the average frequency of the Doppler signal according to one aspect of the present invention.

FIG. 6 illustrates a flow chart of portion of the software which calculates the average frequency (block 318 of FIG. 3). The power vs. frequency is calculated in block 610 as shown in Attachment F. The sum of the power at each frequency is multiplied by the frequency. The result of this multiplication is then divided by the sum of the power at each frequency. All frequency values are linearly normalized such that integers 0–255 represent frequencies 0–10 kiloHertz. The actual average frequency is found by multiplying the normalized average frequency by 40.77 at the end the algorithm.

In addition to the average frequency calculation, this portion of the software performs the signal processing which eliminates the low frequency hump noise discussed above. It has been found that normal Doppler signals contain two specific types of noise which must be eliminated to be able to calculate an accurate rate of flow. The first type of noise is a base line white noise with a bandwidth much larger than any valid Doppler signal. Because it has been shown experimentally that valid Doppler frequencies in the preferred flowmeter system are limited to 0–9 kiloHertz, the software eliminates this base line noise by finding the largest power value between 9 and 10 kiloHertz (above the expected information containing portion of the Doppler signal) and subtracting 612 this value from every input data value of the Doppler signal. The second type of noise is caused by vibrations within the physical sensor/tubing/blood system and is the low frequency hump noise discussed above. This noise appears as a hump which exists over a range of frequencies much lower than the main frequency hump associated with the valid rate of flow data. To eliminate this low frequency hump, first the power spectrum of the signal is determined 614. Next, the average frequency of the raw signal (including the low frequency hump) is determined 616. Next the average power level between the range average frequency/4 (Point A in FIG. 4) and average frequency/2 (Point B in FIG. 4) is determined. Next, the power data values from zero to average frequency/2 are replaced by an exponentially increasing function from zero at zero Hertz to the calculated value of power at the frequency of the average frequency/2, (block 618). A new average frequency value is then calculated from the corrected power distribution data. To eliminate any gross errors caused by a large low frequency hump in the initial calculation, the hump removal process is repeated 620 once. The average frequency value is then returned to the main program 622. The preferred software embodiment of the find average frequency algorithm is shown in Attachment F.

Because the flowmeter of the present invention and the method invoked therein calculates flow rate solely on the basis of frequency, a special case exists at zero rate of flow where the received signal is not a valid Doppler flow signal, but rather purely noise. The noise at zero flow rate is random and will not have an average frequency which is unique to zero flow. Thus, the average frequency calculation algorithm would calculate an erroneous flow rate at zero flow based upon the average frequency received. Although the noise at zero flow is random, it has been roughly characterized as consisting mainly of low amplitude white noise with occasional spikes of normal amplitude, low frequency noise. The terms low amplitude and low frequency are utilized when compared against a valid Doppler signal. If, however, this noise was interpreted as an actual Doppler signal, the average frequency of the white noise could correspond to flow rates typically of from 2.0 to 8.0 liters per minute. The low frequency normal amplitude noise corresponds to flow rates of 0.0–0.3 liters per minute.

Figure 7:
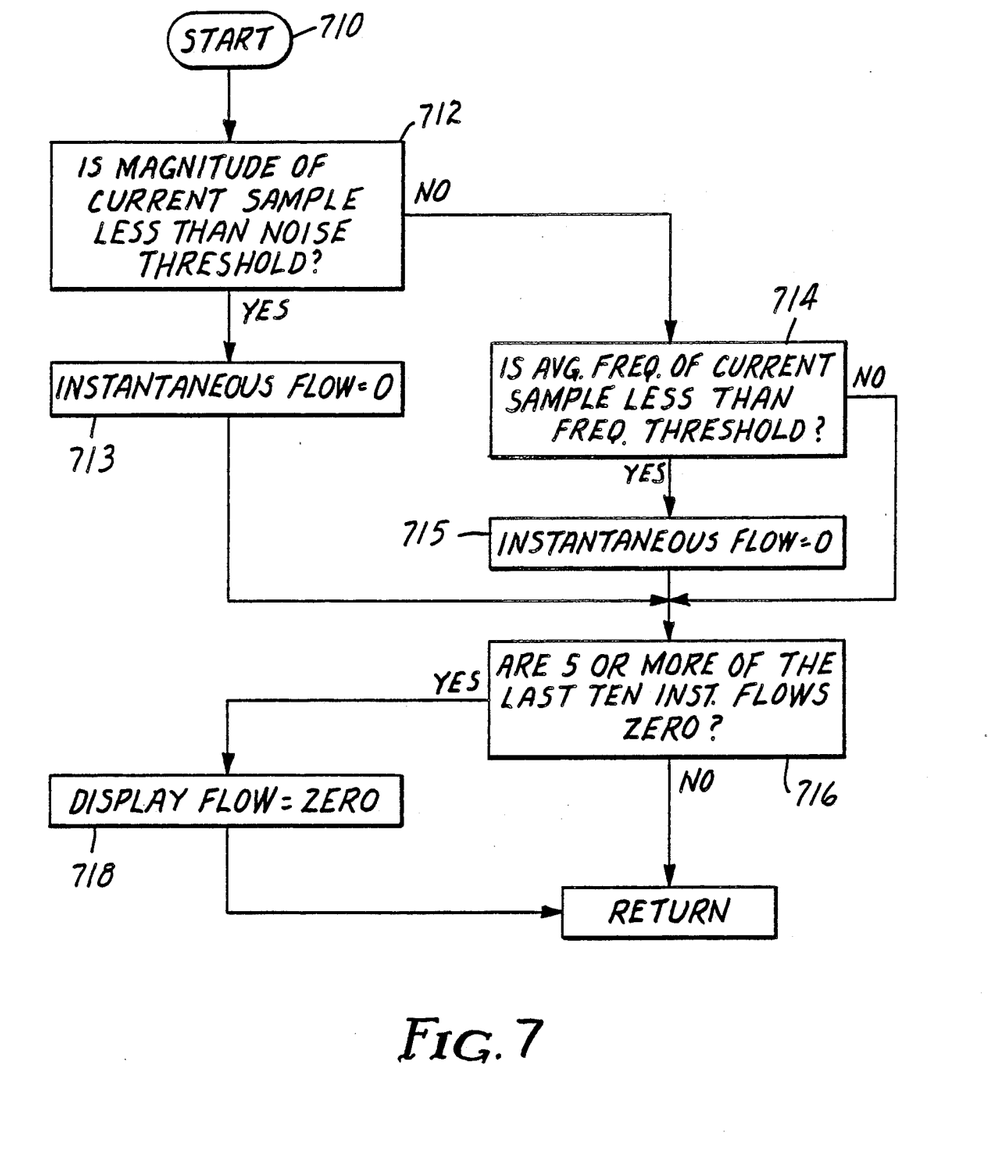
FIG. 7 is a flow chart of a portion of the software algorithm associated with the determination of the special zero flow case according to one aspect of the present invention.

Thus, the software of the preferred embodiment utilized three steps to ensure the start of detection 710 of zero flow as illustrated in FIG. 7. First, the average amplitude of the incoming signal is determined (see block 314 of FIG. 3) and is compared 712 to a predetermined noise threshold. If the current amplitude is below this value (see block 324) then the instantaneous flow rate is set 713 to zero, ignoring the average frequency of the incoming signal. Correct action of this step requires that a safe and predictable margin exists between the amplitude of the zero flow signal and the amplitude of a valid Doppler signal. Second, the instantaneous flow rate is set 715 to zero for all instantaneous flow rates which are less than 0.4 liters per minute (714), i.e, 0.3 liters per minute or less. By doing this, the software ensures that the occasional spikes of low frequency noise will not appear as valid flow readings. Third, the last ten instantaneous flow rates are examined 716, and if a majority of the values are zero, then a zero flow rate is determined to exist 718. Without this third step it would be possible for two or three non-zero instantaneous flow at zero flow to cause an erroneous non-zero flow rate determination as the flow rate otherwise is calculated by averaging the instantaneous flows.

Thus, it can be seen that there has been shown and described a novel Doppler blood flow system and method therefore. It is to be recognized and understood, however, that various changes, modifications and substitutions in the form and the details of the present invention may be made by those skilled in the art without departing from the scope of the invention as defined by the following claims.

What is claimed is:

1. For use in a system having a fluid containing particles flowing at a rate of flow having a value through a tube, a method of determining said value of said rate of flow of said fluid, comprising the steps of:

transmitting an ultrasonic signal through said tube at an oblique angle thereto;

receiving the ultrasonic signal which has been reflected off said particles contained in said fluid creating a received ultrasonic signal having time domain characteristics;

converting said received ultrasonic signal into a frequency domain signal having frequency domain characteristics;

analyzing said frequency domain signal for a low frequency hump;

removing said low frequency hump from said frequency domain signal creating a modified frequency domain signal having an average frequency;

determining the average frequency of said modified frequency domain signal; and calculating said value of said rate of low of said fluid from said average frequency of said modified frequency domain signal using Doppler techniques.

2. For use in a system having a fluid containing particles flowing at a rate of flow having a value through a tube, an apparatus for determining said value of said rate of flow of said fluid, comprising:

an ultrasonic signal transmitter arranged to transmit an ultrasonic signal through said tube at an oblique angle thereto;

a receiver arranged to receive the ultrasonic signal which has been reflected off of said particles contained in said fluid having a received ultrasonic signal having time domain characteristics as an output;

converter means coupled to said receiver and receiving said received ultrasonic signal for converting said received ultrasonic signal into a frequency domain signal having frequency domain characteristics;

analyzer means coupled to said converter means and receiving said frequency domain signal for analyzing said frequency domain signal for a low frequency hump;

signal processing means coupled to said analyzer means for removing said low frequency hump from said frequency domain signal creating a modified frequency domain signal having an average frequency;

determining means coupled to said signal processing means for determining said average frequency of said modified frequency domain signal; and calculating means coupled to said determining means and receiving said modified frequency domain signal for calculating said value of said rate of flow of said fluid from said average frequency of said modified frequency domain signal using Doppler techniques.

* * * * *